United States Patent
Heede et al.

(10) Patent No.: US 9,107,502 B2
(45) Date of Patent: Aug. 18, 2015

(54) SURGICAL SCREW RACK

(71) Applicant: Stryker Trauma GmbH, Schönkirchen (DE)

(72) Inventors: Andreas Heede, Neumünster (DE); Norbert Hentsch, Kiel (DE); Arno Schindler, Brodersdorf (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 13/673,149

(22) Filed: Nov. 9, 2012

(65) Prior Publication Data

US 2013/0119001 A1    May 16, 2013

(30) Foreign Application Priority Data

Nov. 16, 2011    (EP) ...................................... 1100909

(51) Int. Cl.
| | |
|---|---|
| *A47B 96/00* | (2006.01) |
| *A61B 19/02* | (2006.01) |
| *A61B 17/86* | (2006.01) |
| *A61B 19/00* | (2006.01) |

(52) U.S. Cl.
CPC .............. *A47B 96/00* (2013.01); *A61B 17/865* (2013.01); *A61B 19/0256* (2013.01); *A61B 19/34* (2013.01); *A61B 2019/0258* (2013.01)

(58) Field of Classification Search
CPC ............. A61B 19/0256; A61B 17/865; A61B 2019/0258; A61B 19/26; A61B 19/34; A47B 96/00; A47F 7/0028
USPC .............. 206/339, 562, 563, 564; 211/85.13, 211/60.1
See application file for complete search history.

(56) References Cited

U.S. PATENT DOCUMENTS

| | | | | |
|---|---|---|---|---|
| 4,722,440 | A | * | 2/1988 | Johnston ........................ 206/319 |
| 4,955,476 | A | * | 9/1990 | Nakata et al. ................. 206/346 |
| D335,434 | S | | 5/1993 | Someya |
| D356,479 | S | | 3/1995 | Chen |
| 5,469,962 | A | * | 11/1995 | Kitagawa et al. .............. 206/723 |
| 5,579,929 | A | * | 12/1996 | Schwartz ......................... 211/74 |
| 6,019,225 | A | * | 2/2000 | Kalmakis et al. .............. 206/563 |
| 6,286,678 | B1 | * | 9/2001 | Petrek ............................ 206/443 |

(Continued)

FOREIGN PATENT DOCUMENTS

| | | | |
|---|---|---|---|
| DE | 20318732 | U1 | 2/2004 |
| DE | 202007007407 | U1 | 10/2007 |

(Continued)

OTHER PUBLICATIONS

European Search Report dated Mar. 29, 2012 for EP Application No. 11009096.6.

*Primary Examiner* — Stanton L Krycinski

(74) *Attorney, Agent, or Firm* — Lerner, David, Littenberg, Krumholz & Mentlik, LLP

(57) ABSTRACT

A rack for holding at least one surgical screw is described. The rack comprises a body in which at least one bore is provided and at least two support elements surrounding the bore. The support elements protrude from a first level defined on or in the body and are configured to support the screw head on a second level above the first level. The support elements are spaced apart from each other to define spaces therebetween for enabling fluid communication between the surface and the bore. Further, a system is described comprising the above mentioned rack and one or more surgical screws accommodated in the rack.

20 Claims, 5 Drawing Sheets

(56) References Cited

U.S. PATENT DOCUMENTS

| | | | |
|---|---|---|---|
| 6,474,481 B1 * | 11/2002 | Liu | 211/69 |
| 7,350,643 B2 * | 4/2008 | Capanni et al. | 206/370 |
| 7,650,991 B2 * | 1/2010 | Hester et al. | 206/339 |
| 8,061,517 B2 * | 11/2011 | Loeffler et al. | 206/339 |
| 8,490,790 B2 * | 7/2013 | Cocheteux et al. | 206/366 |
| 8,685,068 B2 * | 4/2014 | Sixto et al. | 606/286 |
| 8,821,556 B2 * | 9/2014 | Brand et al. | 606/301 |
| 8,911,233 B2 * | 12/2014 | Moore | 433/163 |
| 2008/0230423 A1 * | 9/2008 | Loeffler et al. | 206/438 |
| 2010/0069969 A1 * | 3/2010 | Ampuero et al. | 606/301 |
| 2011/0108446 A1 | 5/2011 | Bettenhausen et al. | |
| 2011/0288596 A1 * | 11/2011 | Brand et al. | 606/290 |

FOREIGN PATENT DOCUMENTS

| | | | | |
|---|---|---|---|---|
| DE | 102007015154 A1 * | 9/2008 | | |
| EP | 1972290 A2 * | 9/2008 | | A61B 17/86 |
| EP | 1972290 A3 * | 6/2009 | | |
| WO | 2006136291 A1 | 12/2006 | | |
| WO | WO 2010030845 A1 * | 3/2010 | | A61B 17/86 |
| WO | WO 2010097447 A2 * | 9/2010 | | |
| WO | WO 2010097447 A3 * | 11/2010 | | |

\* cited by examiner

SURGICAL SCREW RACK

TECHNICAL FIELD

The present disclosure generally relates to surgical equipment. In particular, a rack for holding at least one surgical screw so as to be accessible by a fluid medium is described.

BACKGROUND OF THE INVENTION

Surgical screws must be cleaned and sterilized before they can be used for surgery. For this purpose, the surgical screws may be stored in a rack. The rack with the screws are generally placed in a cleaning or sterilization chamber into which a fluid cleaning or sterilization medium (such as hot water vapor) may be introduced. To obtain a good cleaning or sterilization result, the surgical screws are preferably arranged in the rack such that the fluid medium can fully access the screws. It is also preferable that the surgical screws can be easily removed from the rack after the cleaning or sterilization operation.

DE 20 2007 007 409 U1 discloses a sterilization rack for surgical screws. The rack comprises a plate with holes for accommodating the screws. Two holes are connected by an elongate slot, wherein the diameter of each hole is larger than the width of the connecting slot. Each hole is adapted to accommodate a shaft of a surgical screw. A head of the surgical screw has a lager diameter than the hole, so that the material surrounding the hole can support the screw head when inserted into the hole.

BRIEF SUMMARY OF THE INVENTION

There is a need for a surgical screw rack that facilitates an efficient cleaning or sterilization of one or more surgical screws accommodated in the rack.

According to one aspect of the present invention, a rack for holding at least one surgical screw so as to be accessible by a fluid medium is provided, wherein the at least one surgical screw has a screw head and a screw shaft. The rack comprises a body having a surface, wherein in the surface at least one bore is provided that is configured to at least partly accommodate the screw shaft. The rack further comprises at least two support elements surrounding the bore, wherein the support elements protrude from a base surface or first level defined on or in the body and are configured to support the screw head on a bearing surface or second level above the first level, and wherein the support elements are spaced apart from each other to define spaces, or guiding spaces, therebetween that enable or guide a fluid communication between the surface and the bore.

The body may be realized in the form of a solid block or plate. The body may have an upper surface and a lower surface. The first level and the second level may be located above the lower surface. In one embodiment, the second level may correspond to the upper surface of the body. In another embodiment, the first level may correspond to the upper surface of the body.

The bore may be realized in the form of a through-bore or otherwise. Moreover, the bore may have a circular or non-circular (e.g., rectangular or oval) cross-section.

The spaces defined between the support elements may be realized in the form of openings. The spaces may stretch in a vertical direction from the first level to the second level or, alternatively, over less than that.

In one embodiment, the spaces can be arranged on opposite sides of the bore. One bore can also have three or more surrounding support elements, wherein a space is defined between each pair of adjacent the support elements. An individual support element may extend (e.g., at least at the second level) in a circumferential direction over at most 45 degrees, 60, degrees, 90 degrees, 120 degrees, 140 degrees, 160 degrees or 170 degrees of a circumference of the bore (or of a surgical screw received therein).

Several bores and support elements can be arranged in a row to accommodate a plurality of surgical screws in the rack. Two bores of the row can have one common, or shared, support element which can at least partly support two screw heads. The row can have a curved or a linear shape.

In one embodiment, a row of bores and support elements can be arranged adjacent to a groove or between two grooves. In the case of multiple grooves, the distance between two neighboring grooves may be less than the extension of a bore (e.g., its diameter) in a direction perpendicular to the grooves.

The one or more grooves may be provided in the surface of the body. Each groove may be configured to guide a fluid medium to the bore via the spaces. Moreover, each groove may have a bottom that defines the first level.

According to another embodiment, multiple parallel rows of bores and support elements can be arranged in or on the body. Each row can be distanced from the adjacent row by a shared (or common) groove.

In another aspect of the present invention, a system comprises one or more surgical screws and a rack, wherein the surgical screws are accommodated in the rack. The support elements can be configured to support the screw head on the second level.

In one embodiment, a screw is received such that in the rack only the screw head is in contact with the body of the rack. A contact portion between the screw head accommodated in the rack and each support element surrounding the bore may be a curved line. For a single support element, the curved line may extend over at most 45 degrees, 60 degrees, 90 degrees, 140 degrees, 160 degrees or 170 degrees of a circumference of the screw head.

According to another aspect of the invention, an orthopedic holding system comprises a rack having a plate body including a base surface, a bearing surface and at least one bore extending through the base and bearing surfaces, the plate body further including at least two support elements protruding upwardly from the base surface to the bearing surface and at least partially surrounding the at least one bore. The system further includes at least one surgical screw having a screw head and a screw shaft, the screw head of the at least one surgical screw having an underside surface. In the system, the at least two support elements are spaced apart from each other to define spaces, or guiding spaces, therebetween that enable or guide a fluid communication into the at least one bore through an opening defined by the base surface, the bearing surface, the at least two support elements and the underside surface of the screw head of the at least one surgical screw when the underside surface of the screw head is in contact with the bearing surface of the plate body and at least a portion of the screw shaft is located within the at least one bore.

BRIEF DESCRIPTION OF THE DRAWINGS

These and other features, aspects and advantages of the present disclosure will become more apparent form the following detailed description taken in conjunction with the accompanying drawings, wherein.

DETAILED DESCRIPTION

Figure 1:
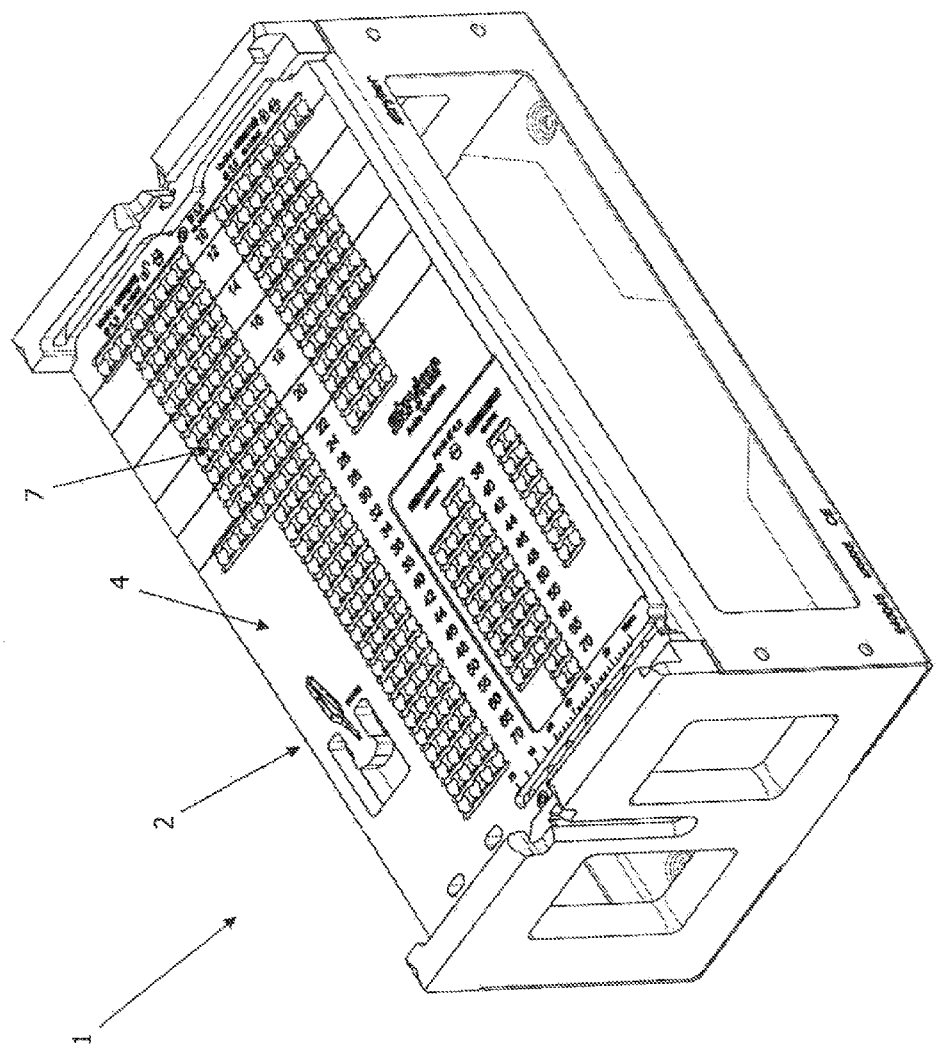
FIG. 1 shows a perspective view of an embodiment of a surgical screw rack.

In the following description, the same reference numerals will be used to denote the same or similar structures in the drawings.

FIG. 1 shows a perspective view of an embodiment of a rack 1 in the form of a tray that is configured to hold surgical screws for sterilization or cleaning purposes. Rack 1 comprises a body 2 in the form of a solid plate in which a plurality of bores 7 is provided. Body 2 has an upper surface 4 bearing (e.g., printed or engraved) information and a lower surface. During surgery, a correct surgical screw has to be chosen for a particular surgical purpose, and the information on upper surface 4 may thus be indicative of at least one of a type, length and diameter of the screw in close association with the screw accommodated in rack 1.

Rack 1 comprises sidewalls with openings that permit an easy access of a cleaning or sterilization medium to the surgical screws accommodated in body 2 in a hanging fashion. Rack 1 is preferably intended to be placed together with the surgical screws accommodated therein in a chamber of a cleaning or sterilization device. Any fluid medium known in the art (such as hot water vapor) may be used for cleaning or sterilization purposes.

Figure 2:
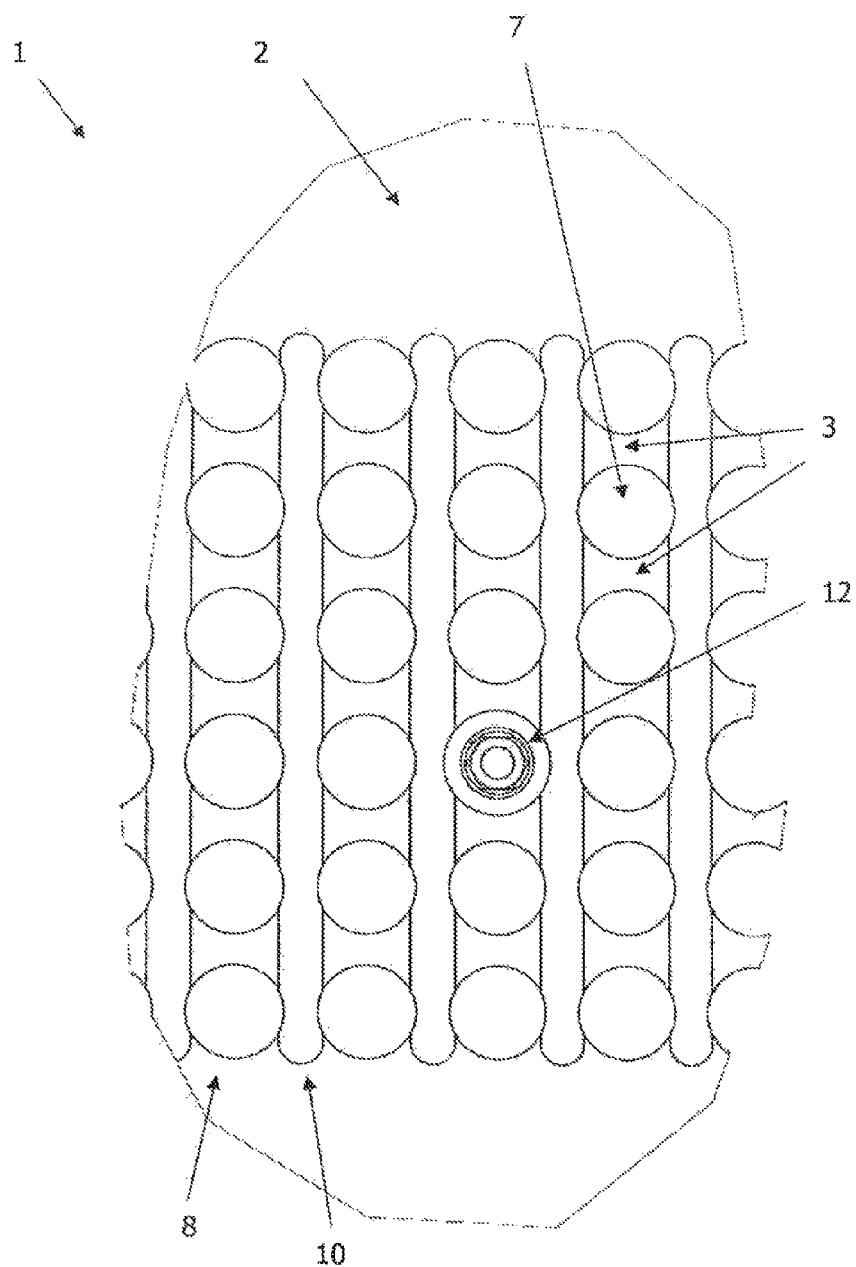
FIG. 2 shows a partial top view of the rack of FIG. 1, wherein one screw is accommodated in one bore of the rack.

FIG. 2 shows a partial top view of body 2 of rack 1 of FIG. 1, wherein one surgical screw 12 is accommodated in one of bores 7 of rack 1. Each bore 7 is surrounded by two support elements 3 which are arranged on opposite sides of bore 7. It is also possible that three, four or more support elements 3 are provided per bore 7.

Figure 3:
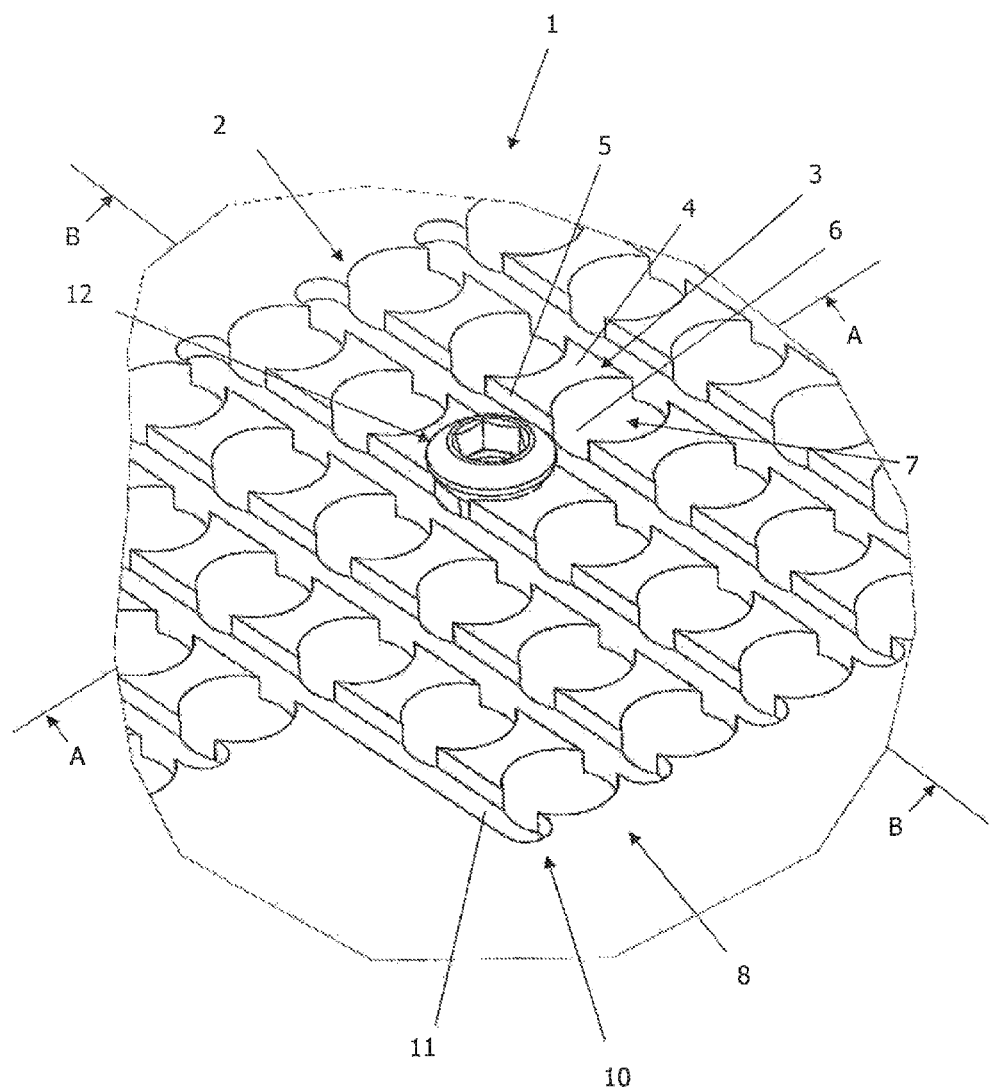
FIG. 3 shows a partial perspective view of the rack of FIG. 1, wherein one screw is accommodated in one bore of the rack.

As shown in FIG. 3, support elements 3 protrude from a base surface or first level within body 2 (i.e., below upper surface 4 but above the lower surface thereof). Upper surface 4 of body 2 (which in the present embodiment coincides with the upper surface of the support element 3) defines a bearing surface or second level which is above the first level. The screw head of the surgical screw 12 is supported in rack 1 only at the second level defined by support elements 3. The first level is defined by a bottom 11 of multiple parallel grooves 10 provided in upper surface 4 of body 2. Each groove is preferably arranged between two rows of bores 7 and support elements 3, as shown in FIGS. 2 and 3.

The height of each support element 3 is defined as the distance between the first level and the second level. Each support element 3 may have the same height (the upper surface thereof being the same distance to the bottom 11 of the groove 10 adjacent to each support element 3). A sidewall 5 of the support element 3 forms the sidewall of the adjacent groove 10.

Two spaces or guiding spaces 6 are defined between the two support elements 3 that surround each bore 7 for enabling a fluid communication between upper surface 4 of body 2 and bore 7. Fluid communication is preferably maintained even when the surgical screw 12 is inserted with its shaft into bore 7 and the screw head abuts support elements 3.

The two spaces 6 are arranged on opposite sides of bore 7. Each space 6 stretches in a vertical direction from the first level to the second level. Hence, the height of each of support elements 3 equals the height of each of spaces 6. The cross-section of each space 6 is substantially rectangular and limited by the surrounding support elements 3 and bottom 11 of groove 10 (and the screw head). However, the cross-section of each space 6 can also be triangular or circular (or have any other shape) as long as a fluid medium can pass through space 6.

In general, each support element 3 has a width which is defined between two sidewalls 5 of support element 3 (each directed toward the respective opposite groove 10, as best shown in FIG. 3) and a length which is defined in a direction parallel to an adjacent groove 10. As shown in FIG. 2, the width of each support element 3 is slightly smaller than the diameter of an adjacent bore 7 (which gives rise to spaces 6 upon milling grooves 10 into body 2).

Each support element 3 extends in a circumferential direction over approximately 135 degrees of a circumference of an individual bore 7. The remaining circumference of bore 7 (of approximately 90 degrees) is occupied by two spaces 6 defined between support elements 3, shared equally. When the circumference of each support element 3 with respect to bore 7 is reduced, the circumference of each space 6 is increased, and vice versa. Thus, when the width of support element 3 becomes smaller, the width of each space 6 defined between support elements 3 increases.

Several bores 7 and support elements 3 arranged in a straight line define one row 8, wherein each row 8 can have in principle also any other shape as long as bores 7 are distanced from each other such that a fluid medium can easily access screws 12 accommodated in bores 7. Several rows 8 are arranged side by side in upper surface 4 of body 2. In the present embodiment, rows 8 of bores 7 and support elements 3 are parallel to each other.

As stated above, several grooves 10 are preferably arranged between parallel rows 8 of bores 7 and support elements 3, wherein each row 8 is situated between two grooves 10. Bores 7 and support elements 3 of one row 8 are preferably arranged in the same order as bores 7 and support elements 3 of an adjacent row 8 such that each support element 3 or each bore 3 faces an adjacent support element 3 or an adjacent bore 3 on the other side of a common groove 10.

The width of each groove 11 arranged between two rows 8 of bores 7 and support elements 3 is approximately half of the diameter of a bore 7 (or more). The central axes of the grooves 10 are substantially perpendicular to the central axes of bores 7. Each bore 7 is in fluid communication with each of the two grooves 10 which surround bore 7 via spaces 6 such that a fluid medium for cleaning or sterilization purposes is enabled to access screw 12 accommodated in bore 7 from both sides via the grooves 10.

Figure 4:
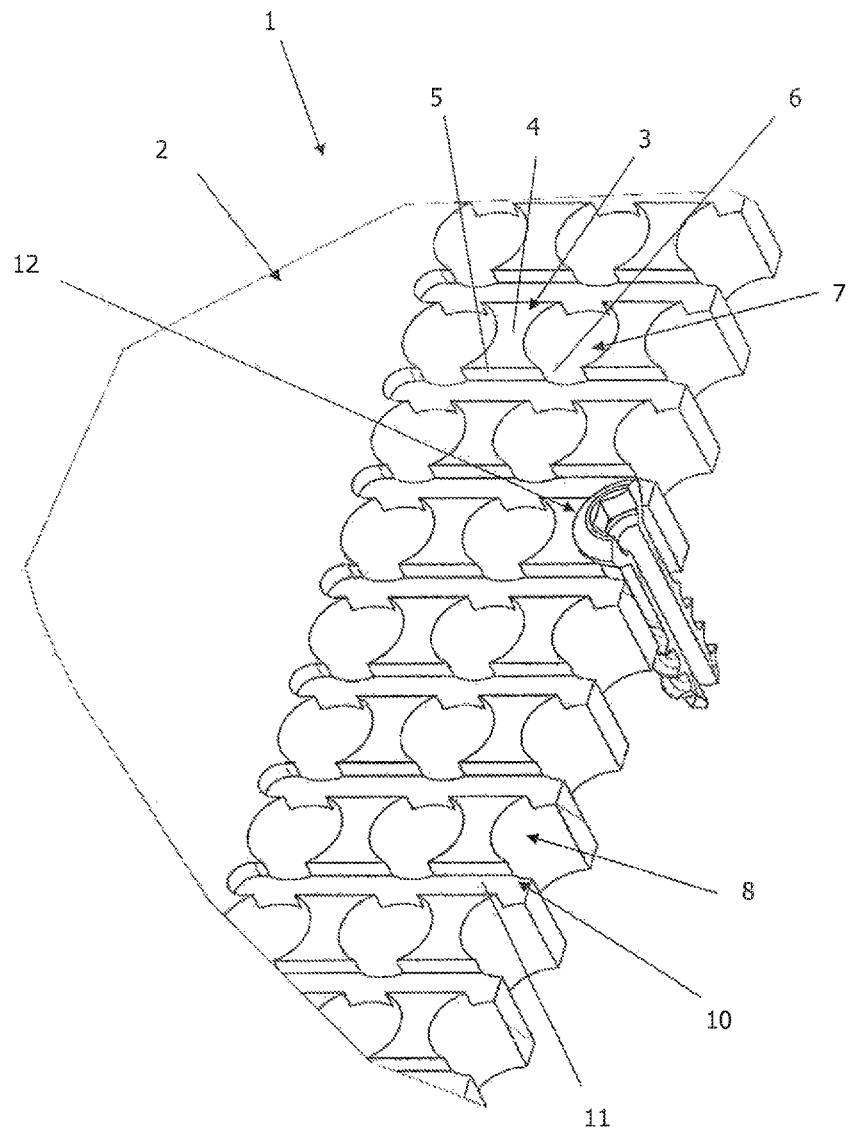
FIG. 4 is a further partial perspective view of the rack, wherein a part of the rack is shown in a sectional view with respect to line A-A of FIG. 3.
Figure 5:
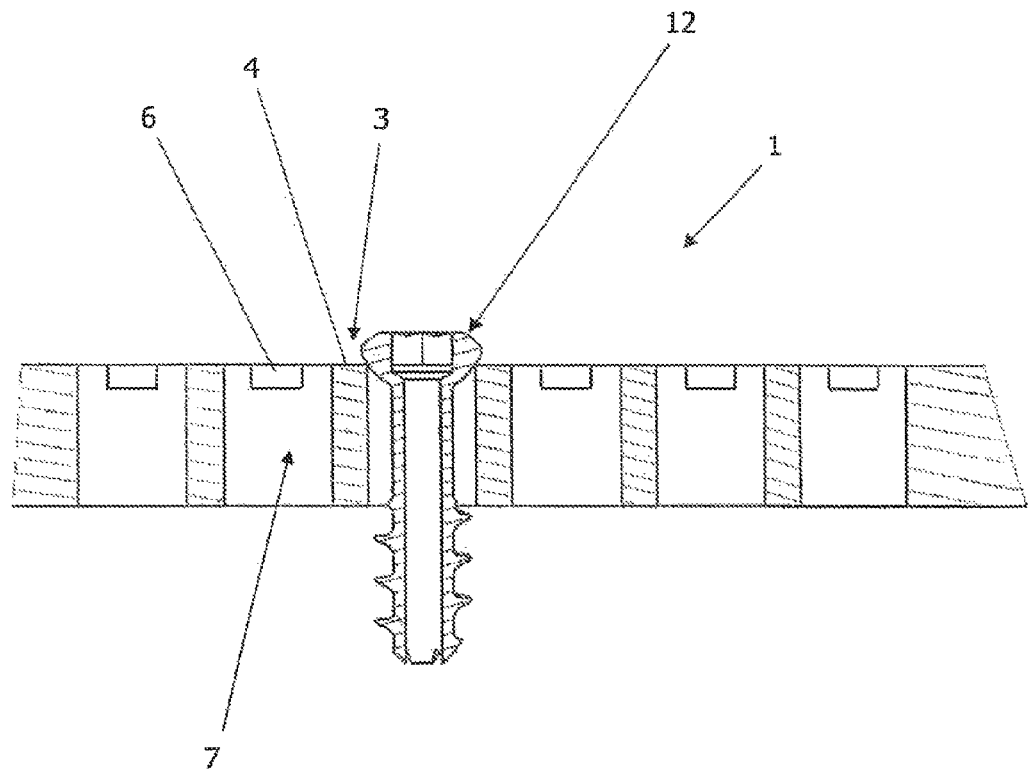
FIG. 5 shows a sectional view of the rack with respect to line B-B of FIG. 3, wherein a screw is accommodated in one bore of the rack.

Each bore 7 is arranged between two support elements 3 such that the upper surfaces of support elements 3 define a support portion to support screw 12 at or near the circumference of bore 7, more particularly at the edges between upper surfaces 4 of support elements 3 and the sidewalls of bore 7, as best shown in FIGS. 4 and 5. Thus, screw 12, in particular the screw head of screw 12, is supported only at these edges. Thereby, the contact portion between screw 12 and each of the two support elements 3 is reduced to a curved line or a circular arc segment, which in turn increases the accessibility of screw 12 by a cleaning or sterilization medium.

Each bore 7 is associated with two spaces 6 which are arranged on opposite sides relative to a central axis of bore 7 and open into the adjacent grooves 10. An adjacent bore 7 which is separated from bore 7 by the common groove 10 also comprises two such spaces 6. These spaces of both bores are arranged in one straight line in a direction which is perpendicular to groove 10. Thus, a fluid medium for cleaning or sterilizing screws 12 accommodated in bores 7 can pass rack 1 not only in longitudinal direction along grooves 10 but also in a transverse direction perpendicularly to grooves 10 through spaces 6.

As best shown in FIG. 5, the diameter of the shaft of screw 12 is smaller than the diameter of bore 7 of rack 1. The diameter of the screw head is larger than the diameter of bore 7 so that screw can be supported at the second level by support elements 3 surrounding bore 7. The only contact portion between screw 12 and rack 1 is between support elements 3 and the screw head. Screw 12 can thus be arranged in a hanging fashion such that the central axis of screw 12 is concentric to the central axis of bore 7 (see FIG. 5).

The height of bore 7 is typically at least half of the length of screw 12 accommodated in bore 7. Bore 7 can have cylindrical sidewalls, or the sidewalls can have a concave or convex shape as long as the distance between the sidewalls of bore 7 and screw 12 is sufficient to allow the fluid medium to access the screw for cleaning or sterilization purposes.

As also shown in FIGS. 3 and 5, the maximum diameter of the screw head is larger than the diameter of bore 7 so that a part of the screw head overlaps with the two grooves which are arranged adjacent to bore 7. Moreover, the screw head is located on the second level defined by the upper surface 4 of the support element 3. Hence, a user or removal instrument (such as tweezers) can easily grip screw 12 via the spaces 6 that are arranged on opposite sides of bore 7.

As has come apparent from the description of an exemplary embodiment, rack 1 is adapted to accommodate screws 12 which can be easily cleaned or sterilized due to the fact that support elements 3 surrounding a bore 7 define spaces or guiding spaces 6 therebetween for enabling or guiding fluid communication between rack surface 4 and bore 7 so that a fluid medium can easily access the screw shaft and also the screw head.

Further, in one embodiment, the only contact area between screw 12 and rack 1 is the edge between support elements 3 surrounding bore 7 and the sidewall of bore 7, so that the fluid medium can access essentially the whole screw 12. A further advantage of the present invention is that due to spaces 6 and the exposed screw head, screw 12 can easily be inserted and picked up by a user or a removal instrument.

While the present disclosure has been described with respect to particular embodiments, those skilled in the art will recognize that the present disclosure is not limited to the specific embodiments described and illustrated therein. It is to be understood that the disclosure is only illustrative. Accordingly, it is intended that the invention be limited only to the scope of the claims attached thereto.

The invention claimed is:

1. An orthopedic holding system comprising:
at least one surgical screw having a screw head and a screw shaft,
a body having a surface, wherein at least one bore extends through the surface along a first axis, the at least one bore configured to accommodate at least a portion of the screw shaft; and
at least two support elements surrounding the at least one bore,
wherein the support elements protrude from a first level defined on or in the body to support the screw head on a second level above the first level along the first axis,
wherein the at least one bore has a sidewall offset from the screw shaft when the screw head is supported on the second level, and
wherein the support elements are spaced apart from each other to define a first guiding space opposite of a second guiding space along a second axis transverse with the first axis, each guiding space stretching between the first level, the at least two support elements, the second level, and the screw head for guiding a fluid communication between the surface of the body and the at least one bore.

2. The system of claim 1, wherein each of the first and second guiding spaces have a rectangular shaped opening stretching from the first level to the second level and spanning between the at least two support elements along the perimeter of the at least one bore.

3. The system of claim 1, wherein each of the at least two support elements extend around at most 170° of a circumference of the at least one bore.

4. The system of claim 1, wherein several of the at least one bore and corresponding at least two support elements are arranged in a row.

5. The system of claim 4, wherein one common support element is arranged between two of the bores.

6. A rack for holding at least one surgical screw so as to be accessible by a fluid medium, each screw having a screw head and a screw shaft, the rack comprising:
a body with a surface and at least one bore extending through the surface along a first axis to accommodate at least a portion of the screw shaft; and
at least two support elements surrounding the at least one bore, each support element protruding from a first level defined on or in the body to support the screw head on a second level above the first level along the first axis,
wherein the at least two support elements are spaced apart from each other to define a first guiding space opposite of a second guiding space along a second axis transverse with the first axis, each guiding space stretching between the first level, the at least two support elements, the second level, and the screw head, and
wherein several of the at least one bore and corresponding at least two support elements are arranged in a row with a linear shape that extends between two grooves, the row and the two grooves being parallel to each other so that each guiding space guides a fluid communication between one of the grooves and corresponding bore.

7. The rack of claim 6, wherein each groove has a bottom that defines the first level.

8. The rack of claim 7, further comprising multiple parallel rows of bores and support elements.

9. An orthopedic holding system comprising:
a rack having a plate body including a base surface opposite of a bearing surface along a first axis and at least one bore extending through the base and bearing surfaces, the plate body further including at least two support elements protruding upwardly from the base surface to the bearing surface and at least partially surrounding the at least one bore about the first axis; and
at least one surgical screw having a screw head and a screw shaft, the screw head of the at least one surgical screw having an underside surface,
wherein the at least two support elements at least partially surrounding the at least one bore are spaced apart from each other to form a first guiding space opposite of a second guiding space along a second axis transverse with the first axis for guiding a fluid communication into the at least one bore, and
wherein each of the first and second guiding spaces is defined by the base surface, the bearing surface, the at least two support elements, and the underside surface of the screw head of the at least one surgical screw when the underside surface of the screw head is in contact with the bearing surface of the plate body and at least a portion of the screw shaft is located within the at least one bore.

10. The system of claim 9, wherein each of the first and second guiding spaces have a rectangular shaped opening stretching from the base surface to the bearing surface and spanning between the at least two support elements along the perimeter of the at least one bore.

11. The system of claim 9, wherein each of the at least two support elements extend around at most 170° of a circumference of the at least one bore.

12. The system of claim 9, wherein several of the at least one bore and corresponding at least two support elements are arranged in a row.

13. The system of claim 12, wherein one common support element is arranged between two of the bores.

14. The system of claim 12, wherein the row has a linear shape.

15. The system of claim 12, wherein the row of bores and support elements is arranged between two grooves and each guiding space guides a fluid communication into the one of the bores from one of the grooves.

16. The system of claim 15, wherein the row of bores and support elements and the grooves are parallel to each other.

17. The system of claim 1, wherein
the sidewall of the at least one bore has a cylindrical shape along the first axis.

18. The system of claim 17, wherein a portion of the sidewall of the at least one bore has a convex shape along the first axis.

19. The system of claim 17, wherein a portion of the sidewall of the at least one bore has a concave shape along the first axis.

20. The system of claim 17, wherein several of the at least one bore and corresponding at least two support elements are arranged in a row with a linear shape that extends between two grooves, the row of bores and support elements and the two grooves being parallel to each other so that each guiding space guides a fluid communication between one of the grooves and corresponding bore.

* * * * *